United States Patent [19]
Dodge et al.

[11] Patent Number: 5,441,947
[45] Date of Patent: Aug. 15, 1995

[54] METHODS OF INHIBITING VASCULAR RESTENOSIS

[75] Inventors: Jeffrey A. Dodge, Indianapolis; Masahiko Sato, Carmel, both of Ind.

[73] Assignee: Eli Lilly and Company, Indianapolis, Ind.

[21] Appl. No.: 111,796

[22] Filed: Aug. 25, 1993

[51] Int. Cl.$^6$ .............................................. A61K 31/56
[52] U.S. Cl. ................................... 514/179; 514/929
[58] Field of Search ............... 514/179, 929; 549/275

[56] References Cited

U.S. PATENT DOCUMENTS 3,668,222 6/1972 Hauser ............................... 549/275

FOREIGN PATENT DOCUMENTS 91-3215423 1/1990 Japan.

OTHER PUBLICATIONS

Kocher, et al., *FEBS*, 291:2, 363–366, (Oct. 1991).
Harrison, *JACC*, 17:6, 71B–76B, (May 1991).
Bankhead, *Medical World News*, 26–34 (Feb. 1991).
Hermans, et al., *American Heart Journal*, 122:1, 171–187 (Jul. 1991).
Liu, et al., *TCM*, 1:3, 107–111 (1991).
*Circulation*, 88:4, Part 2 (Oct. 1993), Abstract 2726.
*JACC*, Feb. 1994:1A–484A, Abstract 829-3.
Dewald, M. B. B., et al., *Br. J. Pharmacol.*, 69(2): 269–270 (1980).
Bonser, R. W., et al., *Br. J. Pharmacol* 103(1): 1237–1241 (1991).
Wiesinger, D., et al., *Experientia* 30(2): 135–136 (1974).
Closse, A. et al., *J. Med. Chem.* 24(12): 1465–1471 (1981).
Reinhold, S. L., et al *The FASEB Journal* 4(2): 208–214 (1990).
Wymann, M. P., et al. *The Journal of Biological Chemistry* 264(27): 15829–15834 (1989).
Dewald, B. et al., *The Journal of Biological Chemistry* 263(31): 16179–16184 (1988).
Haeflinger, W., et al., *Helv. Chem. Acta,* 56(8): 2901–2904 (1973).
MacMillan, J., et al., *J. Chem. Soc.* Perkin I, 2892–2898 (1972).
Abbas, H. K. et al., *Appl. Environ. Microbiol.* 54(5): 1268–1274 (1988).
Nakanishi, S., et al., *J. Biol. Chem.*, 267(4): 2157–2163 (1992).
Ohara-Imaizumi, M., et al., *Biochem. Biophys. Res. Commun.*, 185(3): 1016–1021 (1992).
Coughlin, S. R., et al., *Science*, 243: 1191–1194 (1989).
Baggiolini, M., et al., *Exp. Cell Res.*, 169: 408–418 (1987).
Matter, W. F., et al., *Biochem. Biophys. Res. Commun.* 186(2): 624–631 (1992).
Shibasaki, F., et al., *J. Biol. Chem.*, 266(13): 8108–8114 (1991).
Kaplan, D. R. et al., *Cell*, 50: 1027–1029 (1987).
Valius, M., et al., *Cell*, 73: 321–334 (1993).

*Primary Examiner*—Marianne M. Cintins
*Assistant Examiner*—Kevin E. Weddington
*Attorney, Agent, or Firm*—Steven P. Caltrider; James J. Sales; Gerald V. Dahling

[57] ABSTRACT

Wortmannin and certain of its analogs are inhibitors of restinosis.

2 Claims, No Drawings

METHODS OF INHIBITING VASCULAR RESTENOSIS

BACKGROUND OF THE INVENTION

Vascular restenosis after percutaneous transluminal coronary angioplasty (PTCA) has been shown to be a tissue response characterized by an early and late phase. The early phase occuring hours to days after PTCA is due to thrombosis with some vasospasms while the late phase appears to be dominated by excessive proliferation and migration of smooth muscle cells. In this disease, the increased cell motility and colonization by smooth muscle cells and macrophages contribute significantly to the pathogenesis of the disease. The excessive proliferation and migration of vascular smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology* 8: 369–375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermarts et al., *American Heart Journal* 122: 171–187 (July 1991).

In the pathogenesis of restenosis excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth muscle are useful in the treatment and prevention of restenosis. The present invention provides for the use of wortmannin and certain analogs as restenosis inhibitors.

SUMMARY OF THE INVENTION

The invention provides a method of inhibiting restinosis in a subject comprising administering to said subject a pharmaceutically effective dose of a compound selected from the group of

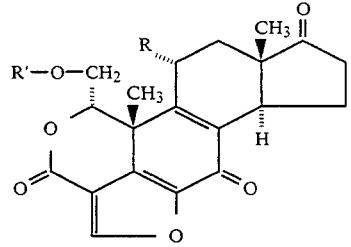

wherein R is hydrogen or acetoxy, and R' is $C_1$–$C_6$ alkyl;

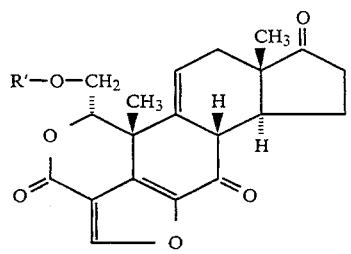

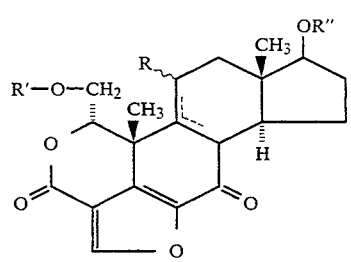

wherein R" is hydrogen, $C_1$–$C_6$ alkyl or

wherein R'" is hydrogen or $C_1$–$C_6$ alkyl;

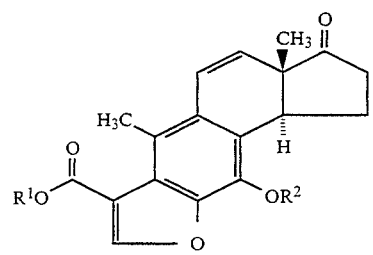

wherein $R^1$ is hydrogen, methyl, or ethyl; and $R^2$ is hydrogen or methyl; or a pharmaceutically acceptable salt of any of the above.

DETAILED DESCRIPTION OF THE INVENTION

The current invention concerns the discovery that wortmannin and its analogs are useful in the inhibition of restinosis. The following compounds are encompassed by the invention:

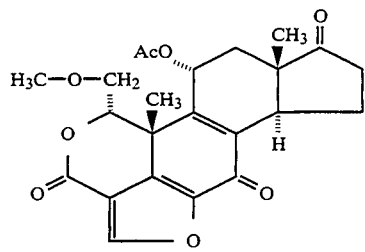

[Wortmannin] (Ia)

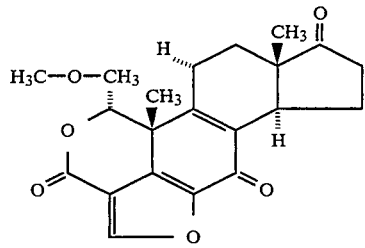

(Ib)

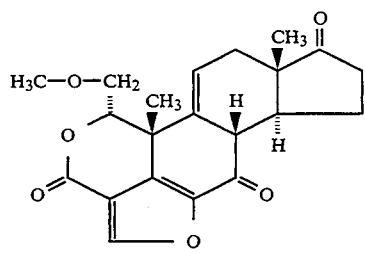

(II)

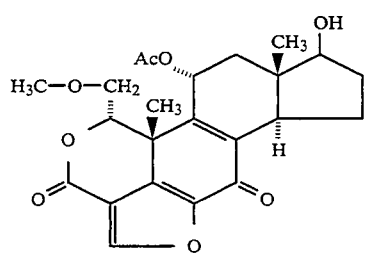

(IIIa)

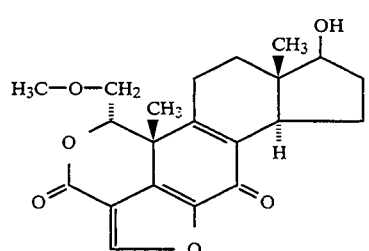

(IIb)

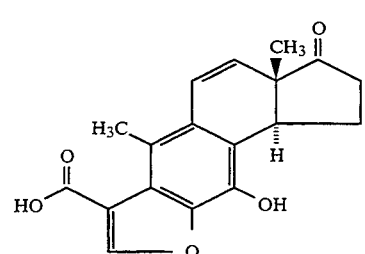

(IVa)

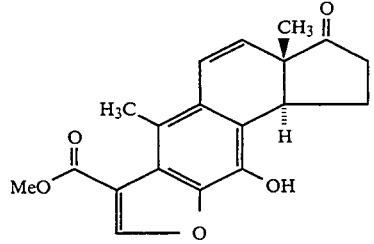

(IVb)

TABLE 1
Wortmannin and Analogs

| Formula Designation | R | R¹ | R² | R" | Trivial Name |
|---|---|---|---|---|---|
| Ia | acetoxy | NA | NA | NA | wortmannin |
| Ib | H | NA | NA | NA | 11-desacetoxywortmannin |
| II | NA | NA | NA | NA | Δ9,11-dehydro-desacetoxywortmannin |
| IIIa | acetoxy | NA | NA | H | 17(α-dihydro-wortmannin |
| IIIb | H | NA | NA | H | 11-desacetoxy-17α-dihydro-wortmannin |
| IVa | NA | H | H | NA | opened A-ring acid of wortmannin |
| IVb | NA | methyl | H | NA | opened A-ring methyl ester of wortmannin |

The biosynthetic production of wortmannin (Ia) is well known in the art and the analogs are synthesized from wortmannin. Typically, wortmannin is produced by the fermentation of any one of a number of previously disclosed microorganisms such as *Talaromyces wortmannin* [Nakanishi, et al., *J. Biol. Chem.*, 267 (4): 2157-2163 (1992)]; and *Penicillium wortmannii, Myrothecium roridium,* and *Fusarium oxysporum* [Abbas, et al., *Appl. Environ. Microbiol.*, 54 (5): 1267-1274 (1988)]. Following fermentation, wortmannin is extracted and purified via known methods.

Preferably, wortmannin is microbially synthesized and isolated in substantially pure form from a fermentation culture identified as A24603.1.

Culture A24603.1 has been deposited in compliance with the Budapest Treaty, and made part of the stock culture collection of the Midwest Area Northern Regional Research Center, Agricultural Research Service, United States Department of Agriculture, 1815 North University Street, Peoria, Ill., 61604. The accession number is NRRL 2112 (*Penicillium duclauxii*).

The permanency of the deposit of this culture at the Midwest Area Northern Regional Research Center at Peoria, Illinois, and ready accessibility thereto by the public will be afforded throughout the effective life of the patent in the event the patent is granted. Access to the culture will be available during pendency of the application under 37 C.F.R. §1.14 and 35 U.S.C. §112. All restrictions on the availability to the public of the culture will be irrevocably removed upon granting of the patent.

Wortmannin is produced by culturing the above-referenced A24603.1 strain under submerged aerobic conditions in a suitable culture medium until a recoverable amount of wortmannin is produced. Wortmannin can be recovered using various isolation and purification procedures understood in the art.

The medium used to grow the A24603.1 culture can be any one of a number of media. For economy in production, optimal yield, and ease of product isolation, however, preferred carbon sources in large-scale fermentation are glucose and soluble starch such as corn starch. Maltose, ribose, xylose, fructose, galactose, mannose, mannitol, potato dextrin, methyl oleate, oils such as soybean oil and the like can also be used.

Preferred nitrogen sources are enzyme-hydrolyzed casein and cottonseed flour, although pepsinized milk, digested soybean meal, fish meal, corn steep liquor, yeast extract, acid-hydrolyzed casein, beef extract, and the like can also be used.

Among the nutrient inorganic salts which can be incorporated in the culture media are the customary soluble salts capable of yielding calcium, magnesium, sodium, ammonium, chloride, carbonate, sulfate, nitrate, zinc, and like ions.

Essential trace elements necessary for the growth and development of the organism also should be included in the culture medium. Such trace elements commonly occur as impurities in other substituents of the medium in amounts sufficient to meet the growth requirements on the organism.

For production of substantial quantities of wortmannin, submerged aerobic fermentation in stirred bioreactors is preferred. Small quantities of wortmannin may be obtained by shake-flask culture. Because of the time-lag in production commonly associated with inoculation of large bioreactors with the spore form of the organism, it is preferable to use vegetative inoculum. The vegetative inoculum is prepared by inoculating a small volume of culture medium with the spore form or mycelial fragments of the organism to obtain a fresh, actively growing culture of the organism. The vegetative inoculum medium can be the same as that used for larger fermentations, but other media are also suitable.

Wortmannin is produced by the A24603.1 organism when grown at temperatures between about 23° and 29° C. Optimum temperature for wortmannin production appears to be about 25° C.

As is customary in submerged aerobic culture processes, sterile air is blown into the vessels from the bottom while the medium is stirred with conventional turbine impellors. In general, the aeration rate and agitation rate should be sufficient to maintain a level of dissolved oxygen of at least 45% of air saturation with an internal vessel pressure of about 5 atmospheres.

Following its production, wortmannin can be recovered from the fermentation medium by methods used in the art. The wortmannin produced during fermentation of the A24603.1 organism occurs mainly in the broth.

Typically, wortmannin can be recovered from the biomass by a variety of techniques. A preferred technique involves filtering whole fermentation broth with a ceramic filter. The filtrate is eluted with an organic solvent such as ethyl acetate and concentrated. The concentrate is suspended in alcohol until crystallization occurs and the solution is filtered, washed and dried. For confirmation, the crystalline material is dissolved in an organic solvent and chromatographed on a reverse-phase silica gel absorbent ($C_8$ or $C_{18}$). Fractions are eluted in an organic-aqueous buffer such as 60% acetonitrile.

11-Deacetoxywortmannin (formula Ib) also is known in the art as are methods for its preparation. Generally, this compound can be biosynthetically produced by fermenting a culture of *Penicillium funiculosum* Thom [see, e.g., Baggolini, et al., *Exp. Cell Res.*, 169: 408–418 (1987)]; but, preferably, is chemically derived from wortmannin by the method disclosed by Haeflinger, et al., *Helv. Chem. Acta*, 56(8): 2901–2904 (1973).

Similarly, the preparation of Δ9,11-dehydrodesacetoxywortmannin (formula II) is known in the art and is described by Haeflinger, et al., supra; and the preparation of compounds of formula IV is described by MacMillan, J., et al., *J. Chem. Soc, Perkin I:* 2892–2898 (1972). The preparation of compounds of the formula III may be prepared by methods known in the art, and are exemplified in the preparation examples, herein. When R″ is

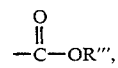

the compounds may be prepared in an analogous fashion as to that described in Ott et al., *J. Am Chem. Soc.* 74, p. 1239 (1952).

For therapeutic treatment of the specified indications, a compound of formula I, II, III or IV may be administered as such, or can be compounded and formulated into pharmaceutical compositions in unit dosage form for parenteral, transdermal, rectal, nasal, local intravenous administration, or, preferably, oral administration. Such pharmaceutical compositions are prepared in a manner well known in the art and comprise at least one active compound selected from the group consisting of compounds of formulae I, II, III, and IV associated with a pharmaceutically carrier. The term "active compound", as used throughout this specification, refers to at least one compound selected from compounds of the formulas or pharmaceutically acceptable salts thereof.

The term "effective amount" as used herein, means an amount of a compound of the present invention which is capable of inhibiting, blocking, or reversing the activation, migration, or proliferation of cells. The activity contemplated by the present methods includes both medical therapeutic and/or prophylactic treatment, as appropriate. The specific dose of a compound administered according to this invention to obtain a therapeutic and/or prophylactic effects will, of course, be determined by the particular circumstances surrounding the case, including, for example, the compound administered, the route of administration, and the condition being treated.

The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way.

The term "inhibiting" includes the administration of a compound of the present invention to prevent the onset of the symptoms, alleviating the symptoms, or eliminating the disease, condition or disorder.

In such a composition, the active compound is known as "active ingredient". In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient of medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water, or the like, and administered intravenously or by injection.

By "pharmaceutically acceptable", it is meant the carrier, diluent or excipient must be compatible with the other ingredients of the formulation and not deleterious to the recipient thereof.

The local delivery of inhibitory amounts of active compound for the treatment of restinosis can be by a variety of techniques which administer the compound at or near the proliferative site. Examples of local delivery techniques are not intended to be limiting but to be illustrative of the techniques available. Examples include local delivery catheters, site specific carriers, implants, direct injection, or direct applications.

Local delivery by a catheter allows the administration of a pharmaceutical agent directly to the proliferative lesion. Examples of local delivery using a balloon catheter are described in EPO 383 492 A2 and U.S. Pat. No. 4,636,195 (Wolinsky, Jan. 13, 1987).

Local delivery by an implant describes the surgical placement of a matrix that contains the pharmaceutical agent into the proliferative lesion. The implanted matrix releases the pharmaceutical agent by diffusion, chemical reaction, or solvent activators. Lange, *Science* 249: 1527–1533 (September, 1990).

An example of local delivery by an implant is the use of a stent. Stents are designed to mechanically prevent the collapse and reocclusion of the coronary arteries. Incorporating a pharmaceutical agent into the stent delivers the drug directly to the proliferative site. Local delivery by this technique is described in Kohn, *Pharmaceutical Technology* (October, 1990).

Another example is a delivery system in which a polymer that contains the pharmaceutical agent is injected into the lesion in liquid form. The polymer then cures to form the implant in situ. This technique is described in PCT WO 90/03768 (Donn, Apr. 19, 1990).

Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is descibed in PCT WO 90/01969 (Schindler, Aug. 23, 1989).

A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, *Science* 249: 1527–1533 (September, 1990) and Mathiowitz, et al., *J. App. Poly. Sci.*, 26:809 (1981).

Local delivery by site specific carriers describes attaching the pharmaceutical agent to a carrier which will direct the drug to the proliferative lesion. Examples of this delivery technique includes the use of carriers such as a protein ligand or a monoclonal antibody. Lange, *Science* 249: 1527–1533 (September).

Local delivery by direct application includes the use of topical applications. An example of a local delivery by direct application is applying the pharmaceutical agent directly to the arterial bypass graft during the surgical procedure.

The following formulation examples are illustrative only and are not intended to limit the scope of the invention in any way. The meaning of the term "active ingredient" is as defined above.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Ethanol | 25.75 |
| Propellant 22 (Chlorodifluoromethane) | 70.00 |

-continued

| | Weight |
|---|---|
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone | 4 mg |
| (as 10% solution in water) | |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient(s) | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 mL |

PREPARATION 1

Fermentation of Culture A24603.1

A. Shake-Flask

The culture A24603.1, either as a lyophilized pellet or as a suspension maintained in liquid nitrogen, is used to inoculate a vegetative medium having the following composition.

| Ingredient | Amount (g/L) |
|---|---|
| Glucose | 10.0 |
| Glycerol | 10.0 |
| Cottonseed Flour[a] | 25.0 |
| Unadjusted pH = 6.3; no adjustment | |

[a]PROFLO Flour (Traders Protein, Memphis, TN).

The inoculated vegetative medium was incubated in a 250 mL wide-mouth Erlenmeyer flask at 25° C. for about 72 hours on a shaker orbiting in a two-inch {5.08 cm) circle at 250 rpm.

B. Tank Fermentation of Culture A24603.1

In order to provide a larger volume of inoculum, 10 mL of incubated shake-flask medium, prepared as described in Section A, was used to inoculate 400 mL of a second-stage vegetative medium having the same composition as described above. This second-stage medium was incubated in a 2-L wide-mouth Erlenmeyer flask at 25° C. for about 23 hours on a shaker orbiting in a two-inch (5.08 cm) circle at 250 rpm.

This second-stage medium (400 mL) was used to inoculate 115 L of sterile production medium having the following composition.

Production Medium

| Ingredient | Amount (g/L) |
| --- | --- |
| Glucose | 25.0 |
| Corn Starch | 10.0 |
| Lexein | 10.0 |
| Enzyme-hydrolyzed casein | 4.0 |
| Blackstrap molasses | 5.0 |
| MgSO₄ (anhydrous) | 5.0 |
| CaCO₃ | 2.0 |
| Deionized H₂O | q.s. to 115 L |
| Unadjusted pH = 6.8; no adjustment. | |
| Antifoam agent added: SAG 471[b] (0.2 gm/L). | |

[a]NZ Amine A (Sheffield Chemical Co., Norwich, NY).
[b]SAG 471 (Union Carbide, Sistersville, WV).

The inoculated production medium was allowed to ferment in a 115-L stirred fermentation tank for 4–5 days at a temperature of about 25° C. A dissolved oxygen level of about 45% of air saturation was maintained, as was a low rpm (180–330) in the stirred vessel.

PREPARATION 2

Isolation and Purification of Wortmannin

Fermentation broth from Preparation 1 was filtered through a ceramic filter (Membralox Systems, Illinois Water Treatment, Rockford, Ill.) to yield 175 L of filtrate containing wortmannin. The pH of the filtrate was adjusted to about 3.9 with 5N HCl. The filtrate was then eluted three times with one-half volumes of ethyl acetate to give a combined volume of 207 L which was concentrated to 6 L in vacuo.

The 6 L of ethyl acetate concentrate was further concentrated in vacuo to form a dark brown viscous oil to which 500 mL of methanol was added. The mixture was swirled until the resulting crystallization was complete, filtered, briefly washed with cold methanol and dried in vacuo to give 20.4 g of wortmannin.

The methanol supernatant was reconcentrated in vacuo to form a viscous oil, dissolved in 180 mL of chloroform and applied to a 12×20 cm column of Woelm Grade 62 silica in chloroform. 5.0 L of chloroform wash was concentrated in vacuo to form a brown oil which was then dissolved in 250 mL of warm methanol. The resulting crystals were collected after 18 hours, via filtration, giving 4.2 g of wortmannin. The crystallization procedure was repeated on the remaining supernatant, yielding an additional 1.9 g of wortmannin. The identity of wortmannin was confirmed by HPLC.

PREPARATION 3

17α-Dihydrowortmannin

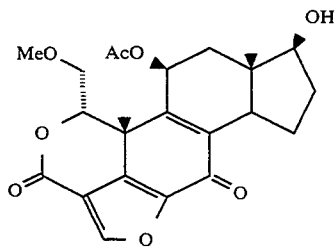

[301497]

To a solution of wortmannin (100 mg) stirring in THF at −78° C. was added diisobutylaluminum hydride (0.4 mL of a 1.0M solution in toluene, 0.4 mmol). After 0.5 h, the reaction was quenched with saturated aqueous NaHCO₃. The mixture was then warmed to room temperature and extracted with CH₂Cl₂. The combined organic extracts were washed with brine and dried (HgSO₄). The crude material was purified by radial chromatography (SiO₂, 4 mm, 9:1 EtOAc/Hexanes) to give 17α-dihydrowortmannin as an off-white powder.

$^1$H NMR (300 MHz, CDCl₃) 8.22 (s, 1H), 6.10 (m, 1H), 4.76 (dd, 1H), 3.88 (t, 1H), 3.44 (dd, 1H), 3.20 (s, 3H), 2.95 ($\frac{1}{2}$ ABq. 1H), 2.75 (m, 1H), 2.62 ($\frac{1}{2}$ ABq, 1H), 2.52 (m, 1H), 2.10–2.30 (m, 4H), 1.4–1.7 (m), 0.85 (s, 3H), MS FD+ 431, IR (Cell, CDCl₃), 1751, 1680 cm−1).

PREPARATION 4

11-Desacetoxy-17α-dihydrowortmannin

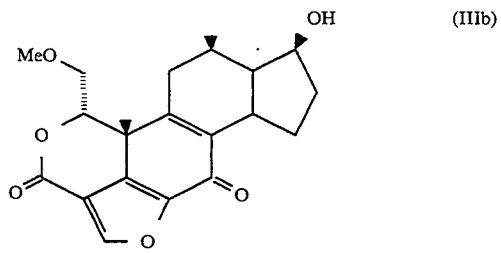

[303015]

To a solution of compound Ib (15 mg) (prepared via the method of Haefloger, W.; Hauser, D. *Helv. Chim. Acta,* 56, 2901, (1973)) stirring in THF at −78° C. was added diisobutylaluminum hydride (0.1 mL of a 1.0M solution in toluene). After 1h, the reaction was quenched with saturated aqueous NaHCO₃. The mixture was then warmed to room temperature and extracted with CH₂Cl₂. The combined organic extracts were washed with brine and dried (MgSO₄). The crude material was purified by radial chromatography (SiO₂, 1 mm, 9:1 EtOAc/Hexanes) to give the titled product as a tan powder.

$^1$H-NMR (300 MHz, CDCl₃) 8.19 (s, 1H), 4.81 (t, 1H), 3.80 (t, 1H), 3.15 (s, 3H), 1.7 (s, 3H), 0.7 (s, 3H). MS FAB+ 373.3.

Compounds of the invention were tested for impact on smooth muscle cell chemotaxis using a model AB96 Neuro Probe ® 96 well chemotaxis chaser. References citing use of this assay are Falk et al., "A 48 Well Micro Chemotaxis Assembly for Rapid and Accurate Measurement of Leukocyte Migration", *J. of Immunological Methods,* 33, pp 239–247 (1980); Harvath et al., "Rapid Quantification of Neutrophil Chemotaxis", *J. of Immunological Methods,* 37, pp 39–45 (1980); Richards et al., "A Modified Microchamber Method for Chemotaxis and Chemokinesis", *Immunological Conn.* 13(1), pp 49–62 (1984); Harvath et al., "Two Neutrophil Populations in Human Blood with Different Chemotactic Activities", *Inf. and Immunity,* 36(2), pp. 443–449 (1982). This chamber is available from Neuro Probe, Inc., P.O. Box 400, Cabin John, Md. 20818.

The chamber consists of a top plate, a bottom plate, a gasket and a polyvinyl pyrrolidone-free polycarbonate filter. The 96 lower plate wells are filled with ~30 μl of media (for control) or PDGF-BB at 10 ng/ml as an inducer, or chemoattractant. The 8 μm pore filter is soaked in 0.5N acetic acid overnight and coated with collagen at 100 μg/ml in 0.1N acetic acid for 2 days. The filter is then dried in a hood. The filter is then installed on the bottom plate, followed by the gasket. The top plate is then placed on the gasket, forming the top wells. In the top wells, smooth muscle cells are placed with the compounds to be tested at specified concentrations in around 225 μl volume. The smooth muscle cells are plated at a density of $0.5 \times 10^6$ cells/mi. The chamber is incubated at 37° C., 5% $CO_2$ for four hours, and at the end of this time the upper well-cells are scraped off. The lower well cells are fixed, stained, and the absorbance is read. The results are in Table 2.

Based on these assays, the half maximal inhibiting concentrations ($IC_{50}$) to inhibit smooth muscle cell chemotaxis are: IIIA, IC50=0.02 μM; Wortmannin, IC50=0.03 μM; Ib IC50=0.2 μM; II IC50=0.2 μM; IVb, IC50=10 μM; and IVa, IC50>10 μM.

TABLE 2

| Compound | | Degree of Cell Migration |
|---|---|---|
| Blank | | 0.000 |
| PDGF, 10 ng/ml | | 0.046 |
| Colchicine, 1 μm | | 0.000 |
| Ia, Wortmannin | 0.3 μm | −0.001 |
| | 0.1 μm | 0.006 |
| | 0.03 μm | 0.020 |
| Ib | 1 μm | −0.010 |
| | 0.3 μm | 0.015 |
| | 0.1 μm | 0.040 |
| | 0.03 μm | 0.044 |
| | 1 μm | 0.000 |
| | 0.3 μm | 0.015 |
| | 0.1 μm | 0.028 |
| | 0.03 μm | 0.036 |
| IIIA | 0.03 μm | −0.010 |
| | 0.1 μm | −0.010 |
| | 0.03 μm | 0.002 |
| | 0.01 μm | 0.033 |
| IVA | 10 μm | 0.04 |
| IVB | 10 μm | 0.026 |

We claim:

1. A method of inhibiting restenosis in a subject following coronary angioplasty, atherectomy, or arterial bypass graft surgery comprising administering to said subject a pharmaceutically effective dose of a compound selected from the group of

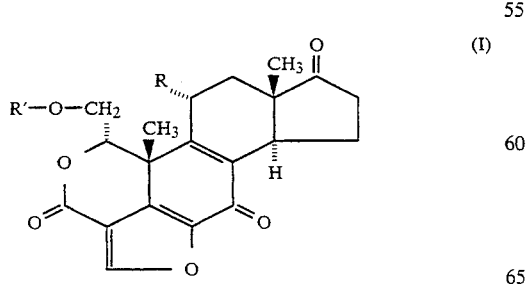

wherein R is hydrogen or acetoxy, and R' is $C_1$–$C_6$ alkyl;

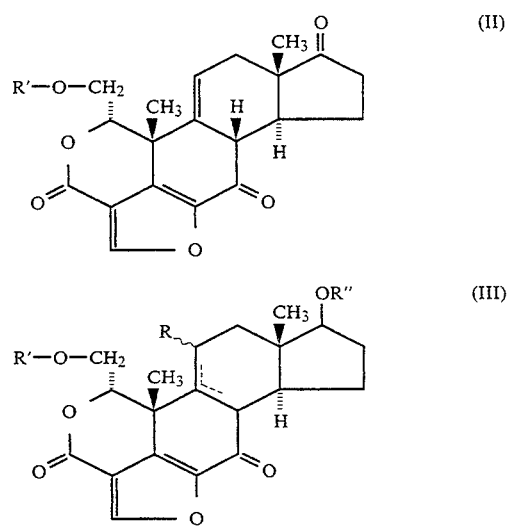

wherein R and R' are as defined above and R" is hydrogen, $C_1$–$C_6$ alkyl or

wherein R''' is hydrogen or $C_1$–$C_6$ alkyl; and

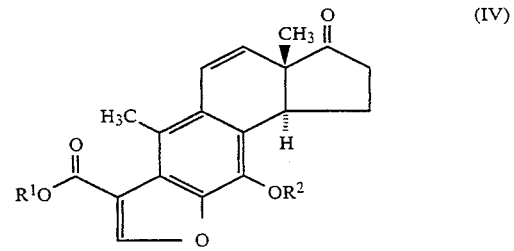

wherein $R^1$ is hydrogen, methyl, or ethyl; and $R^2$ is hydrogen or methyl; or a pharmaceutically acceptable salt of any of the above.

2. The method of claim 1 wherein the compound is selected from

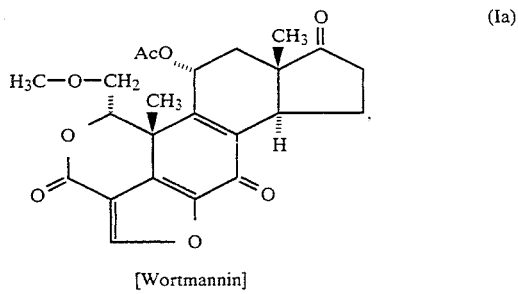

[Wortmannin]

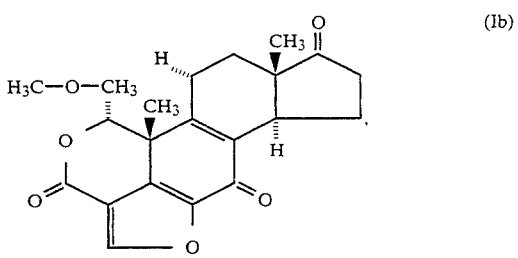

-continued
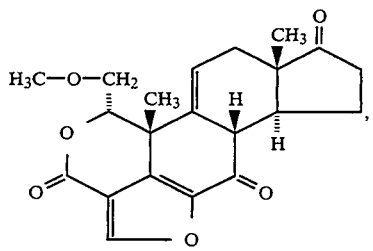
(II)
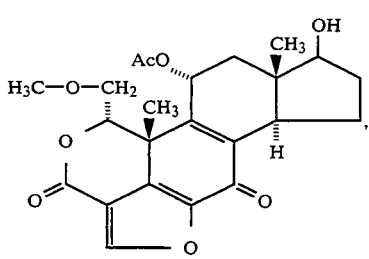
(IIIa)
-continued
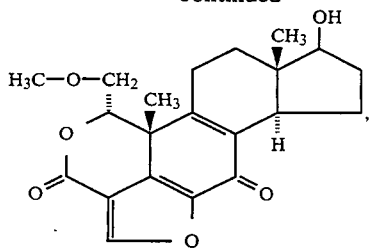
(IIb)
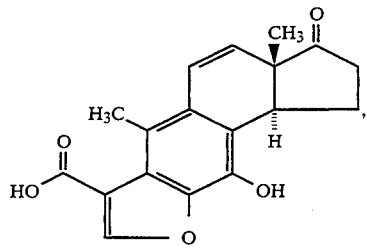
(IVa)
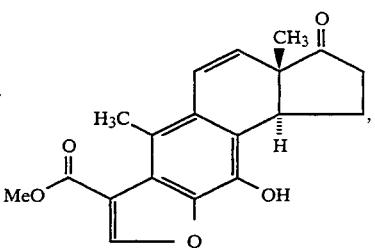
(IVb)
or a pharmaceutically acceptable salt thereof.
* * * * *

UNITED STATES PATENT AND TRADEMARK OFFICE
CERTIFICATE OF CORRECTION

PATENT NO. : 5,441,947
DATED : August 15, 1995
INVENTOR(S) : Jeffrey A. Dodge and Masahiko Sato It is certified that error appears in the above-indentified patent and that said Letters Patent is hereby corrected as shown below:

Column 14, Line 62, Figure (1b), read:

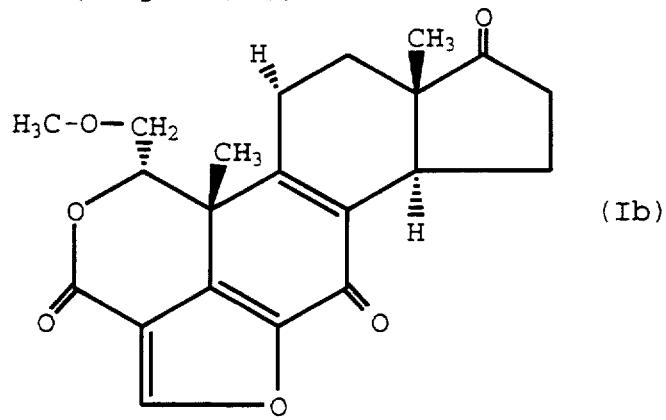

(Ib)

Column 16, Line 5, "(IIb)" should read --(IIIb)--

Signed and Sealed this

Twenty-sixth Day of December, 1995

Attest:

BRUCE LEHMAN

*Attesting Officer*  *Commissioner of Patents and Trademarks*